United States Patent [19]

Albino et al.

[11] Patent Number: 5,145,773

[45] Date of Patent: Sep. 8, 1992

[54] METHOD TO DETECT SENSITIVITY TO ALPHA-INTERFERON THERAPY

[75] Inventors: Anthony P. Albino, New York; David M. Nanus, New Rochelle; Neil H. Bander; Lawrence M. Pfeffer, both of New York, all of N.Y.

[73] Assignee: Sloan-Kettering Institute for Cancer Research, New York, N.Y.

[21] Appl. No.: 357,075

[22] Filed: May 25, 1989

[51] Int. Cl.[5] ............................................ G01N 33/574
[52] U.S. Cl. .................................. 435/7.23; 436/504; 436/804; 436/813
[58] Field of Search ............... 435/7.23, 172.2, 240.27; 436/518, 519, 504, 548, 813, 800; 424/85.7; 530/387

[56] References Cited

U.S. PATENT DOCUMENTS 4,713,352 12/1987 Bander et al. ...................... 436/548

OTHER PUBLICATIONS

Nanus et al "Absence of gp 160 Expression in Renal Carcinomas Predicts Sensitivity to Alpha-Interferon," Proceedings of the American Assoc. for Cancer Research vol. 3, Mar. 1989 Abstract 1546 p. 389.
Quesada et al "Renal Cell Carcinoma: Antitumor Effects of Leukocyte Interferon" Cancer Research vol. 43 (Feb. 1983) pp. 940-947.

Primary Examiner—Esther L. Kepplinger
Assistant Examiner—Carol E. Bidwell
Attorney, Agent, or Firm—John P. White

[57] ABSTRACT

This invention provides a method of detecting sensitivity to alpha-interferon therapy which comprises contacting a sample with a monoclonal antibody under conditions so as to form an antibody-antigen complex, detecting the complex so formed, and thereby detecting sensitivity to alpha-interferon.

5 Claims, 3 Drawing Sheets

SK-RC (A) ● (top)
SK-RC (B) ▲ (top)
SK-RC (C) -O--
SK-RC (D) -△--
SK-RC (E) ◆
SK-RC (F) ◇
SK-RC (G) ▼
SK-RC (H) ▽
SK-RC (I) ■
SK-RC (J) □
SK-RC (K) ▲
SK-RC (L) △
SK-RC (M) ●
SK-RC (N) ○

Figure 2

RENAL CARCINOMAS + INTERFERON
IN VITRO RESULTS

| | CELL LINES TESTED | SENSITIVE | RESISTANT |
|---|---|---|---|
| gp160 – | 8 | 7 | 1 |
| gp160 + | 6 | 0 | 6 |

RENAL CARCINOMAS + INTERFERON
IN VIVO RESULTS

|        | CELL LINES TESTED | SENSITIVE | RESISTANT |
|--------|-------------------|-----------|-----------|
| gp160 −| 4                 | 4         | 0         |
| gp160 +| 4                 | 1         | 3         |

METHOD TO DETECT SENSITIVITY TO ALPHA-INTERFERON THERAPY

BACKGROUND OF THE INVENTION

Patients with metastatic renal cell carcinoma have a very poor prognosis with a five-year survival rate of <5%. Recently, biological therapies (e.g., interferons, interleukins, monoclonal antibodies) have demonstrated moderate anti-tumor activity in this disease. In some studies, over 30% of patients treated with alpha-interferons have exhibited a major response. Interferon treatment is associated with moderate toxicity, however, at present it is impossible to predict which subset of patients will benefit from interferon therapy. Monoclonal antibodies, while of limited therapeutic benefit, have been useful in diagnostic studies. Some of these antibodies identify as assortment of glycoproteins of varying molecular weights expressed on the cell surface of renal cancers.

SUMMARY OF THE INVENTION

This invention provides a method of detecting sensitivity to alpha-interferon therapy which comprises contacting a sample with a monoclonal antibody under conditions so as to form an antibody-antigen complex, detecting the complex so formed, and thereby detecting sensitivity to alpha-interferon.

BRIEF DESCRIPTION OF THE FIGURES

FIG. 2 summarizes the in vitro results for fourteen (14) cultured cell lines assayed for sensitivity to alpha-interferon.

FIG. 3 summarizes the in vivo results of ten nu/nu mice inoculated subcutaneously with cells of one of four different gp negative renal cancer cell lines that exhibited interferon sensitivity in vitro.

DETAILED DESCRIPTION OF THE INVENTION

Figure 1:
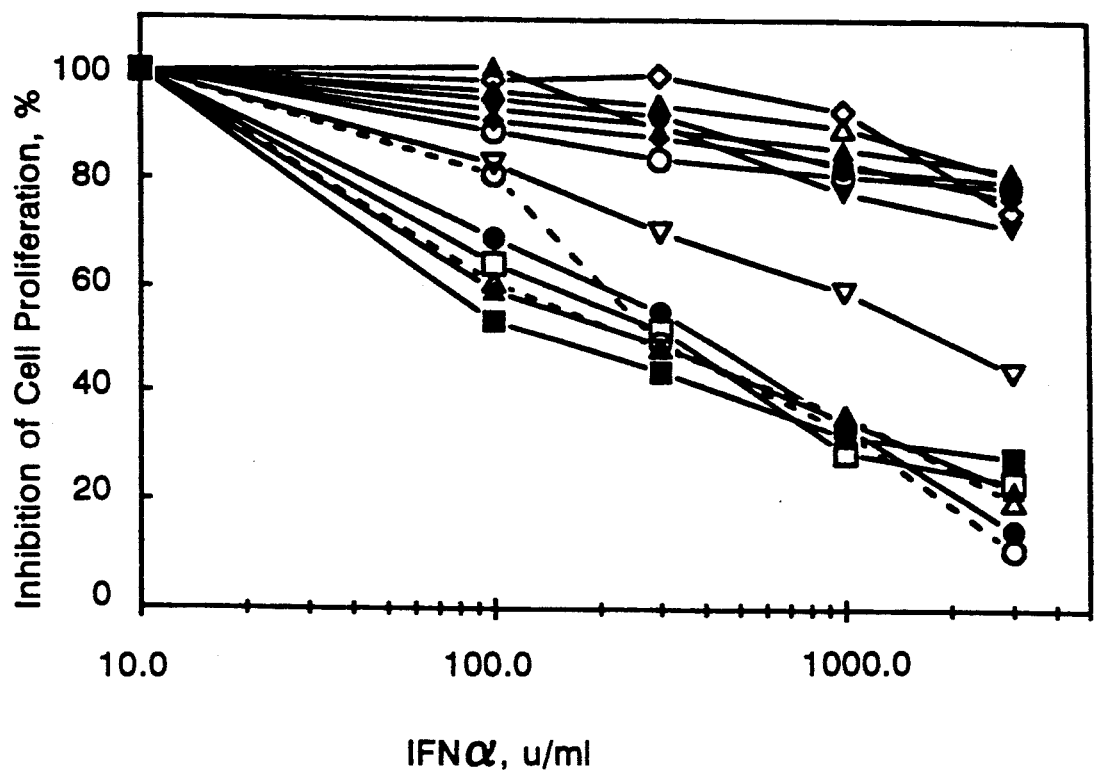
FIG. 1 shows the results of fourteen (14) cultured renal cell lines assayed for sensitivity to alpha interferon.

This invention provides a method of detecting sensitivity to alpha-interferon therapy which comprises contacting a sample with a monoclonal antibody under conditions so as to form an antibody-antigen complex, detecting the complex so formed, and thereby detecting sensitivity to alpha-interferon. The alpha-interferon therapy for which this method is useful comprises any alpha-interferon therapy which uses an alpha-interferon molecule or derivative thereof which has an anti-proliferative effect on malignant cells, i.e. natural or recombinant alpha-interferon molecules or a derivative thereof. The monoclonal antibody which may be useful in the practice of this invention is any monoclonal antibody which recognizes an epitope of the gp 160 cell-surface antigen. As can be seen below, the monoclonal antibody designated F33 (ATCC No. HB 10155), has been shown to be one such antibody which recognizes the gp 160 cell-surface antigen. The hybridoma which produces the monoclonal antibody F33 has been deposited pursuant to the Budapest Treaty On The International Recognition Of The Deposit Of Microorganisms For The Purposes Of Patent Procedure with the Patent Culture Depository of the American Type Culture Collection (ATCC), 12301 Parklawn Drive, Rockville, Md. 20852 U.S.A. under ATCC Accession No. HB 10155.

The samples which may be usefully employed in the practice of this invention comprise any malignant cells or tissue, e.g. human malignant cells or tissue, to which alpha-interferon has been shown effective as a therapy. Such malignant cells or tissue may comprise, but is not limited to, carcinoma cells or tissue, such as human renal carcinoma cells or tissue.

Experimental Method

As will be shown below, absence of expression by renal cell carcinomas of a specific surface glycoprotein of 160 kilodaltons molecular weight (gp 160) predicts for sensitivity to the anti-proliferative effect of alpha interferon.

In the initial experiments, 14 cultured renal cancer cell lines were assayed for sensitivity to the inhibitory action of recombinant alpha-interferon on cell proliferation, and correlated the results with gp 160 expression. (See FIG. 1.) Briefly, cell lines were plated at $1 \times 10^5$ cells per 25 cm$^2$ flask in Dulbecco's MEM. After one day, the cells were fed with medium containing alpha-interferon (Interferon-Alpha Con1; AMGEN, Inc.) ("IFN") at varying concentrations (100 u/ml; 300 u/ml; 1000 u/ml; 3000 u/ml). Control cultures did not receive interferon. Six days following interferon addition, the cells were washed with phosphate buffered saline and harvested by trypsinization for five minutes at 37° C. The cells were counted using a Coulter counter, and ratios of the cell number on day 6 were expressed as a percentage of the ratio to the untreated control cultures. Proliferation of six cell lines expressing gp 160 was not inhibited by IFN at concentrations as high as 3000 units/ml. In contrast, proliferation of size of eight cell lines lacking expression of gp 160 was markedly inhibited (>50%) by IFN, at concentration ranging from 100 to 1000 units/ml.

In a second set of experiments using an animal mode, a group of ten nu/nu mice was inoculated subcutaneously with 10$^6$ cells of one of four different gp 160 negative renal cancer cell lines that exhibited interferon sensitivity in vitro. In each experiment, five of the mice were subsequently treated with 10$^6$ units of interferon intraperitioneally three times a week (Monday, Wednesday, Friday), and five mice received no interferon. Tumors appeared at the site of inoculation in mice not receiving interferon within five to 45 days. In contrast, mice treated with interferon exhibited a marked sensitivity, as demonstrated by either no tumor formation, and/or a decrease in tumor size. Two groups ten nu/nu mice were also inoculated subcutaneously with 10$^6$ cells of one of two different gp 160 positive renal cancer cell lives that exhibited interferon resistance in vitro. Tumors appeared at the sites of inoculation in all mice regardless if interferon therapy within 10 to 40 days. These data suggest that the absence of gp 160 expression by renal carcinomas predicts for sensitivity to the anti-proliferation effect of alpha interferon.

Experimental Discussion

Assessment of gp 160 expression can be performed in most pathology departments using simple techniques (i.e., immunoperioxidase staining on frozen tissue from primary or metastatic renal cancers). With this information, a prediction could prospectively be made as to which patients with renal cancer are most likely to have a clinical response to therapy with alpha-interferon.

This information would of great benefit to patient care. First, patients with metastatic disease whose tumors lacked expression of gp 160 (gp 160 negative) would be treated as first line with interferon with the best chances of obtaining a complete or partial response. Likewise, patients whose tumors showed gp 160 expression (gp 160 positive) would receive other therapies (i.e., interleukin) as initial treatment. This would avoid the morbidity of interferon therapy in patients who would not receive clinical benefit, and allow treatment as first line with the most active agents when the odds of responding to any therapy are highest. Secondly, patients with surgically removed primary gp 160 negative tumors with a high probability of relapse (e.g. advanced local disease, regional nodal involvement) could receive interferon in an adjuvant setting, with the likelihood of eradicating any microscopic disease not removed by the surgeon. This would translate into improved survival and cure for thousands of patients a year. Finally, as a prototype method of predicting therapeutic response by assessment of surface antigen expression, this technique would open a new avenue of diagnostic techniques. Predicting likelihood of response will enable the physician to treat the cancer patient with the best possible therapy for his or her individual tumor, with the highest likelihood of benefit to the patient.

What is claimed is:

1. A method of screening malignant renal cells or malignant renal tissues for sensitivity to alpha-interferon therapy which comprises contacting a sample of the malignant renal cells or malignant renal tissues with monoclonal antibody F33 produced by hybridoma ATCC No. HB 10155 under suitable conditions, such that the monoclonal antibody specifically binds to a gp 160 cell-surface antigen to form an antigen-antibody complex, detecting the presence of any complex so formed, the presence of any complex being predictive that the sample of malignant renal cells or malignant renal tissues will not be sensitive to alpha-interferon therapy.

2. The method of claim 1, wherein the monoclonal antibody is labelled with a detectable marker.

3. The method of claim 2, wherein the detectable marker is a radioisotope.

4. The method of claim 1, wherein the malignant renal cells or malignant renal tissues are renal carcinoma cells or renal carcinoma tissues.

5. The method of claim 4, wherein the renal carcinoma cells or renal carcinoma tissues are human renal carcinoma cells or human renal carcinoma tissues.

* * * * *

UNITED STATES PATENT AND TRADEMARK OFFICE
CERTIFICATE OF CORRECTION

PATENT NO. : 5,145,773
DATED : September 8, 1992
INVENTOR(S) : Anthony P. Albino, et al.

It is certified that error appears in the above-indentified patent and that said Letters Patent is hereby corrected as shown below:

On Column 1, line 4 please add:

—      This invention was made with support under Grant No. CA-08748 from the National Institutes of Health, U.S. Department of Health and Human Services. Accordingly, the United States Government has certain rights in the invention. —

Signed and Sealed this

Seventh Day of February, 1995

*Attest:*

BRUCE LEHMAN

*Attesting Officer*      *Commissioner of Patents and Trademarks*